US007987544B2

(12) United States Patent
Stoeffler et al.

(10) Patent No.: US 7,987,544 B2
(45) Date of Patent: Aug. 2, 2011

(54) BRUSHHEAD ATTACHMENT SYSTEM FOR A POWER TOOTHBRUSH

(75) Inventors: Friedrich Stoeffler, Kirkland, WA (US); Craig K. Black, Snohomish, WA (US); Daniel J. Greene, Seattle, WA (US); Ronald C. Lilley, Federal Way, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1198 days.

(21) Appl. No.: 10/562,271

(22) PCT Filed: Jun. 21, 2004

(86) PCT No.: PCT/IB2004/050952
§ 371 (c)(1),
(2), (4) Date: Dec. 22, 2005

(87) PCT Pub. No.: WO2005/000149
PCT Pub. Date: Jan. 6, 2005

(65) Prior Publication Data
US 2007/0214587 A1    Sep. 20, 2007

Related U.S. Application Data

(60) Provisional application No. 60/483,214, filed on Jun. 27, 2003.

(51) Int. Cl.
*A61C 17/22* (2006.01)
*A61C 17/34* (2006.01)
(52) U.S. Cl. ....................................................... 15/22.1
(58) Field of Classification Search ................... 15/22.1, 15/28
See application file for complete search history.

(56) References Cited

U.S. PATENT DOCUMENTS

| 3,588,936 | A | | 6/1971 | Duve |
| 3,927,435 | A | | 12/1975 | Moret et al. |
| 5,077,855 | A | * | 1/1992 | Ambasz ..................... 15/22.1 |
| 5,142,723 | A | * | 9/1992 | Lustig et al. ................ 15/22.1 |
| 5,365,627 | A | | 11/1994 | Jousson et al. |
| 5,875,510 | A | | 3/1999 | Lamond et al. |
| 6,308,359 | B2 | * | 10/2001 | Fritsch et al. ............... 15/22.1 |
| 2003/0115695 | A1 | | 6/2003 | Lev et al. |
| 2003/0163881 | A1 | * | 9/2003 | Driesen et al. .............. 15/22.1 |
| 2003/0204924 | A1 | | 11/2003 | Grez et al. |

FOREIGN PATENT DOCUMENTS

| DE | 2014278 | 10/1971 |
| DE | 9108243 U | 10/1991 |
| FR | 2780254 A1 | 12/1999 |

* cited by examiner

*Primary Examiner* — Randall Chin
(74) *Attorney, Agent, or Firm* — Daniel Sheridan

(57) ABSTRACT

The attachment system includes a brushhead assembly having a spring/carrier combination which comprises a spring assembly and a separate carrier assembly, adapted to mate as a combination with a receiving portion, in the form of a cup member, at the top of the handle of the toothbrush. The spring/carrier combination includes a slot which mates snugly with a vertical rib on the inside surface of the cup member, and further includes a portion which opposes the slot on the spring/carrier combination which mates snugly with a cut-out portion in the cup member, to prevent rotational movement of the brushhead relative to the handle. The spring/carrier assembly further includes two opposing spring finger elements, wherein the lower ends of the spring fingers fit into corresponding openings in opposing sides of the cup member when the spring/carrier assembly is operatively positioned in the cup member, tending to prevent translational movement of the brushhead relative to the handle.

9 Claims, 6 Drawing Sheets

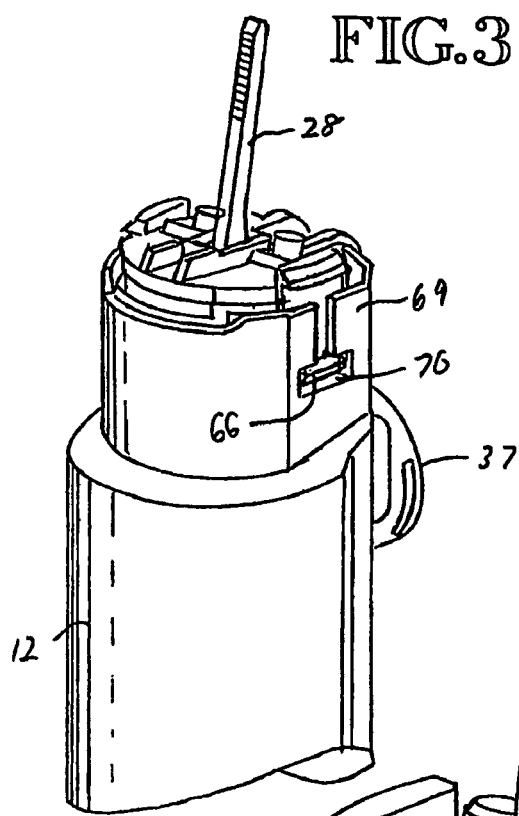
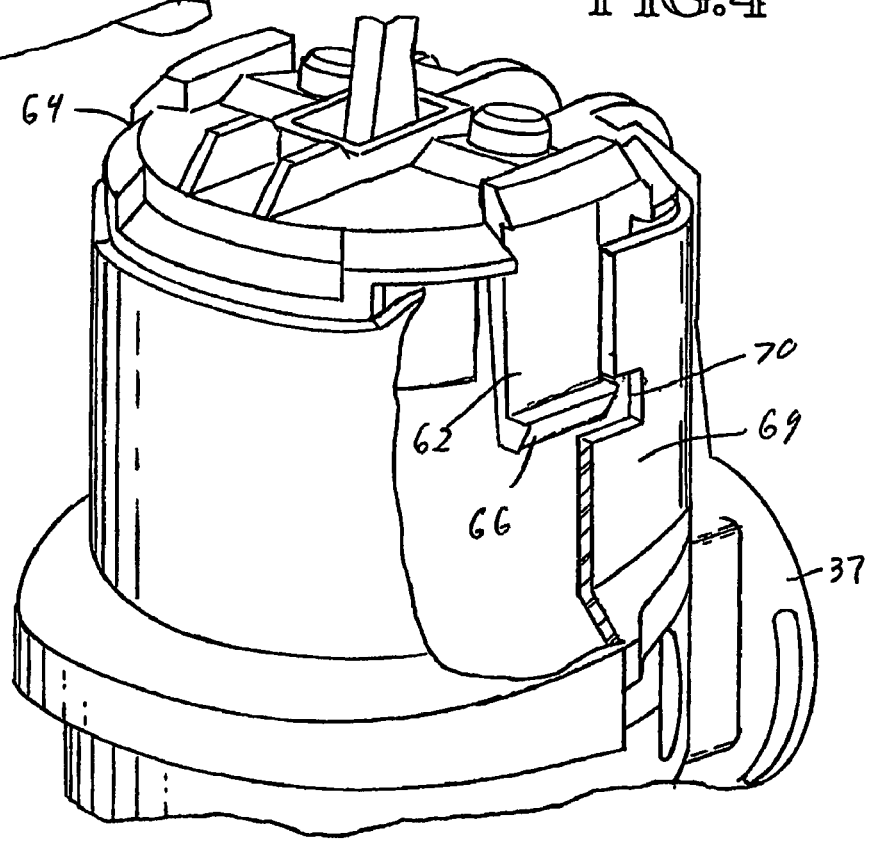

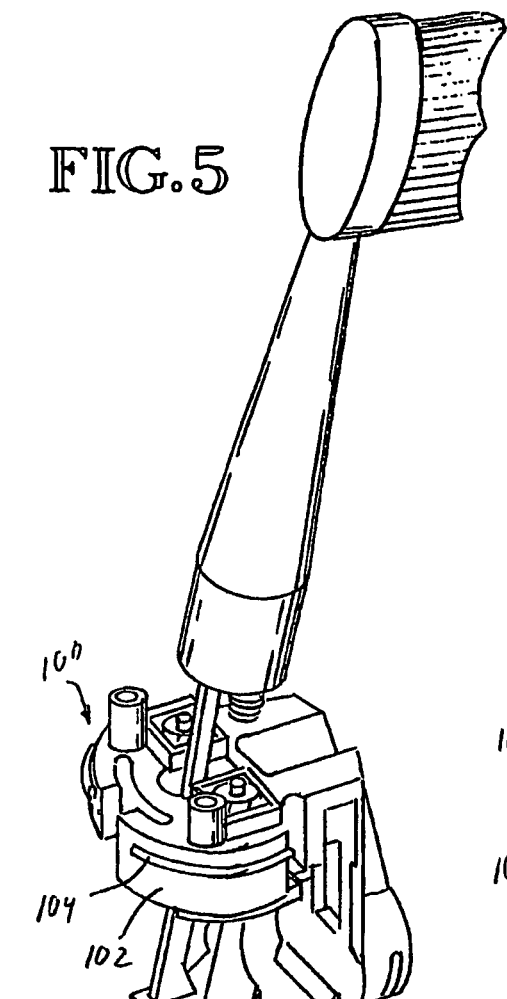
FIG. 5
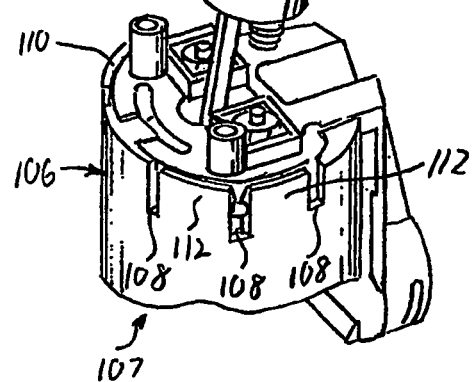
FIG. 6
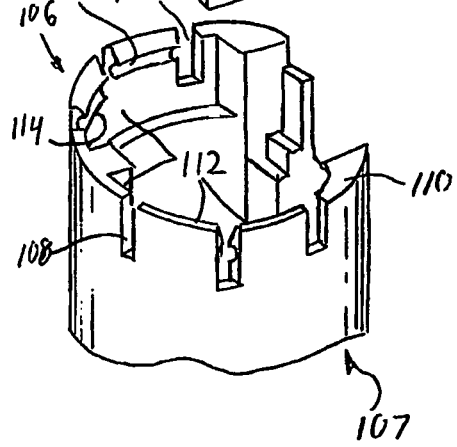
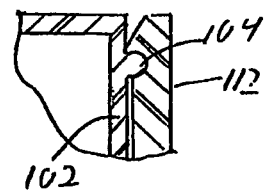
FIG. 7

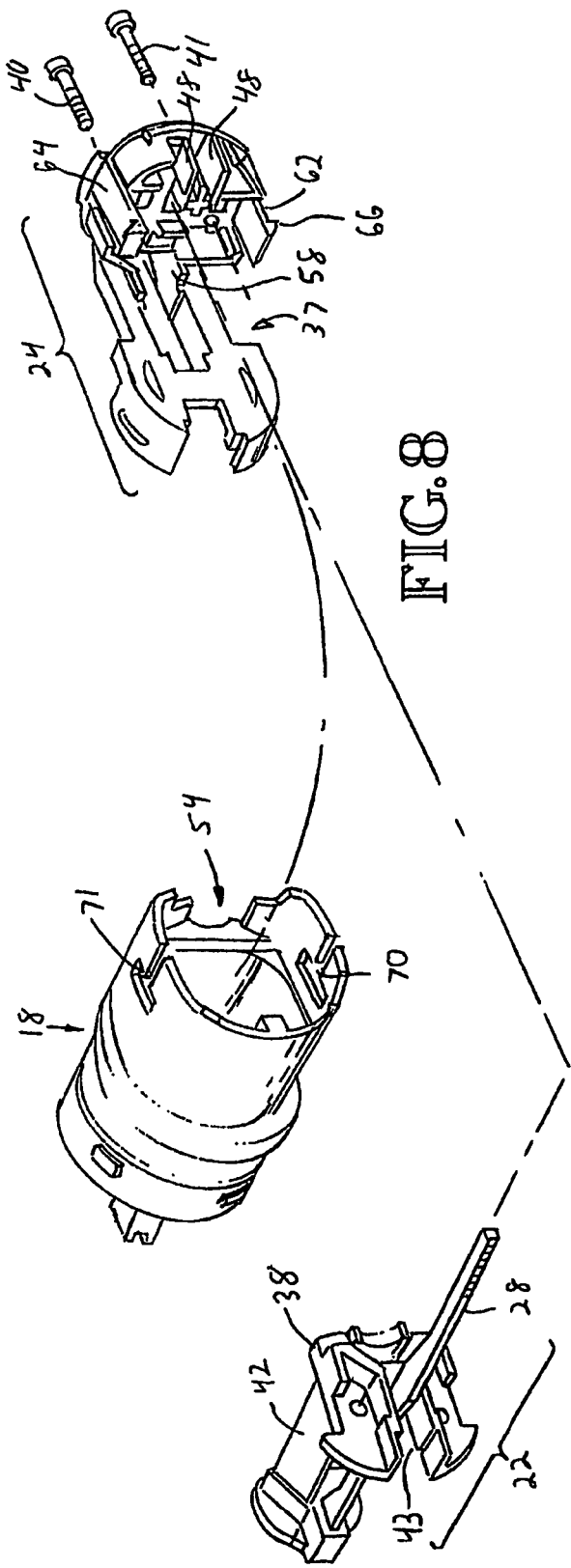
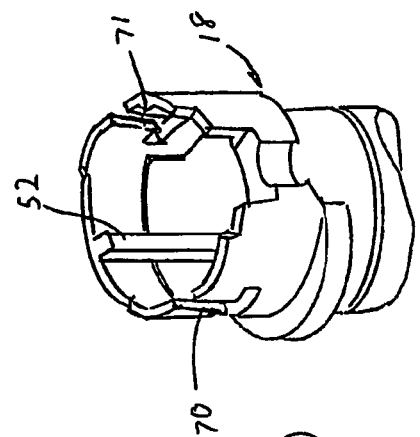
FIG. 8
FIG. 9

BRUSHHEAD ATTACHMENT SYSTEM FOR A POWER TOOTHBRUSH

CROSS REFERENCE TO RELATED APPLICATION

This application claims the benefit of U.S. Provisional Application Ser. No. 60/483,214 filed Jun. 27, 2003, which the entire subject matter is incorporated herein by reference.

TECHNICAL FIELD

This invention relates generally to power toothbrushes with removable brushhead assemblies, and more particularly concerns an attachment system for such a brushhead assembly.

BACKGROUND OF THE INVENTION

In many power toothbrushes, a brushhead assembly portion thereof is twisted or screwed on to a handle portion, by a rotational action, to secure the brushhead to the handle and provide a unitary appearance/operation for the toothbrush. Such an arrangement typically protects against both rotation of the brushhead assembly relative to the handle in operation of the toothbrush, as well as translational (longitudinal) action of the brushhead assembly relative to the handle. Both of these actions are undesirable, since they decrease the operating efficiency and reduce the beneficial results of the toothbrush, as well as increasing the noise of the toothbrush in operation.

In some cases, however, due to the relative physical dimensions of a particular brushhead assembly and its associated handle, or for other reasons, the brushhead assembly must be moved directly onto and off of the handle, i.e. without rotating/twisting any part of the brushhead assembly onto/off the handle. It is still important that the attaching structure be designed to prevent both rotational and translational motion of the brushhead relative to the handle during operation of the toothbrush.

SUMMARY OF THE INVENTION

Accordingly, the present invention is a brushhead assembly attachment system for a power toothbrush, wherein the power toothbrush includes a handle to which the brushhead assembly is removably attached, the handle having a receiving portion, the brushhead attachment system comprising: a brushhead assembly, which includes a force conversion assembly, adapted for mating with the receiving portion of the handle, including a mounting shaft on which is positioned a bristle unit for brushing teeth, wherein the force conversion assembly is adapted and arranged to convert a driving force into a movement of the mounting shaft to move the bristle unit in a manner to accomplish cleansing of the teeth, wherein the attachment system includes a first connection arrangement between the force conversion assembly and the receiving portion of the handle for preventing rotational movement of the brushhead assembly relative to the handle; wherein the force conversion assembly further includes at least one engaging member which, when the brushhead assembly is operatively positioned in the receiving portion, extends at least partially into an opening in the receiving portion of the handle, which tends to prevent translational movement of the brushhead assembly relative to the handle during operation of the toothbrush; wherein the attachment system is configured and arranged such that the brushhead assembly is removed from the handle or inserted into the handle linearly, directed toward and away from the handle, without rotation of the brushhead assembly being necessary to tighten the brushhead assembly onto the handle or loosen it therefrom.

BRIEF DESCRIPTION OF THE DRAWINGS

FIGS. 2, 3 and 4 are perspective views showing the combination of the spring assembly, carrier assembly and handle portions of the toothbrush of FIG. 1.

FIG. 4 is a perspective view of a portion of the brushhead attachment assembly of the present invention.

FIG. 5 is an exploded view of an alternative embodiment of the present invention.

FIG. 6 is an assembled perspective view of the elements of FIG. 5.

FIG. 7 is a cross-sectional view of a portion of the embodiment of FIGS. 5-6.

FIGS. 8-11 are additional views of the toothbrush of FIGS. 1-4.

BEST MODE FOR CARRYING OUT THE INVENTION

Figure 1:
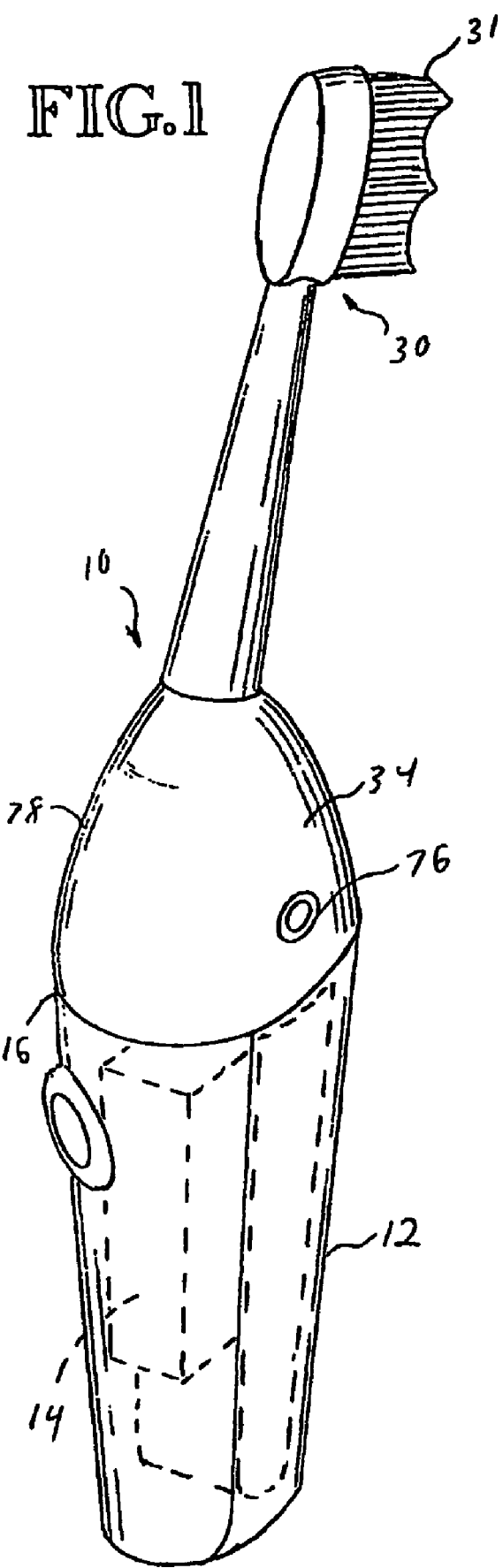
FIG. 1 is a perspective view showing a power toothbrush incorporating the brushhead assembly attachment system of the present invention.
Figure 2:
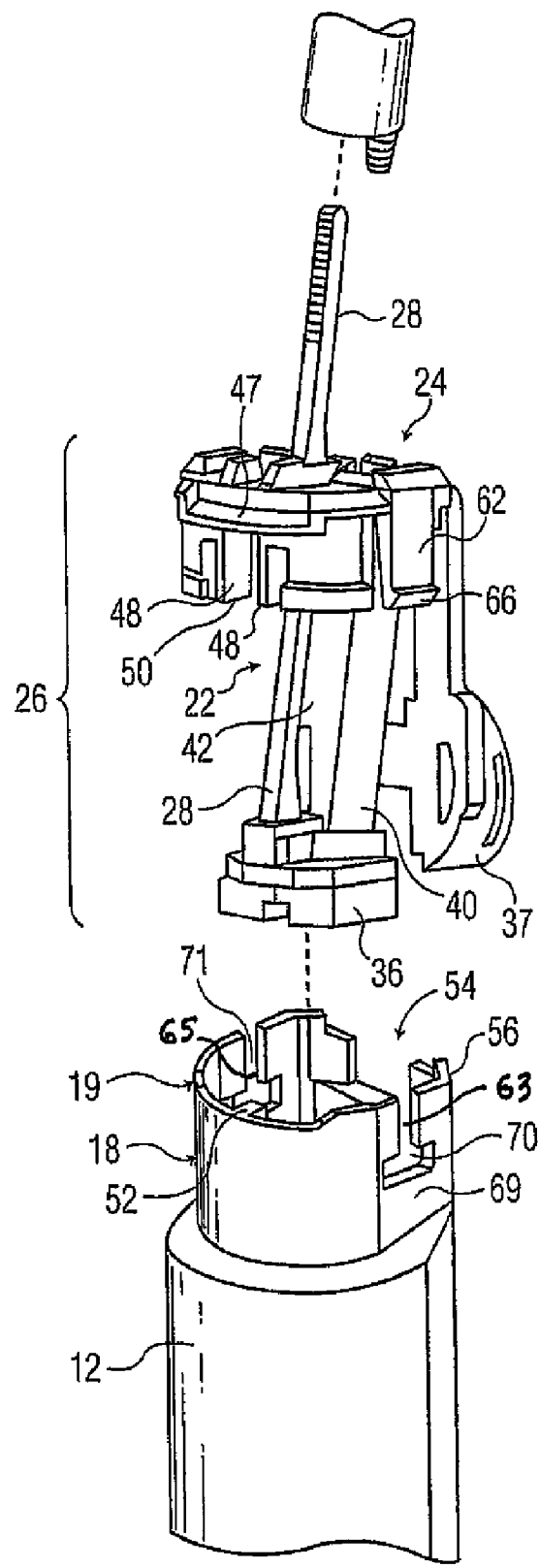
FIG. 2 is a partially exploded view showing the attachment system of the present invention.
Figure 10:
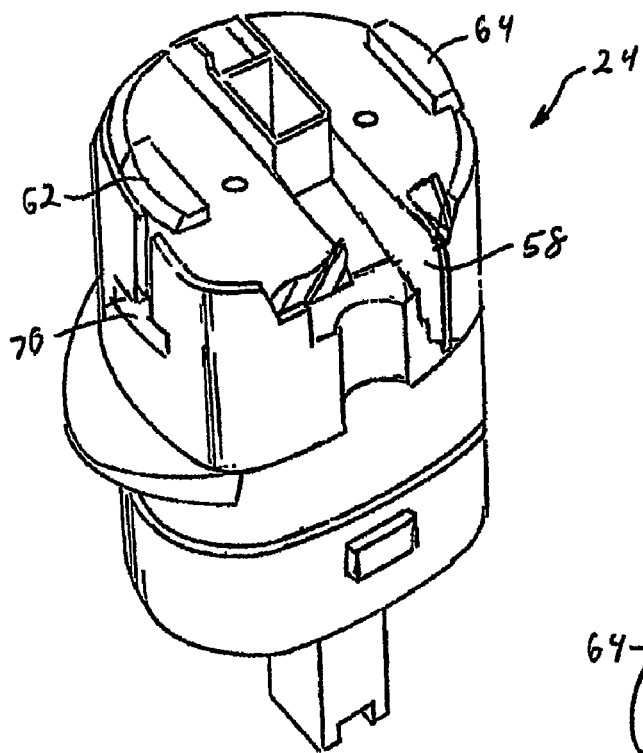
Figure 11:
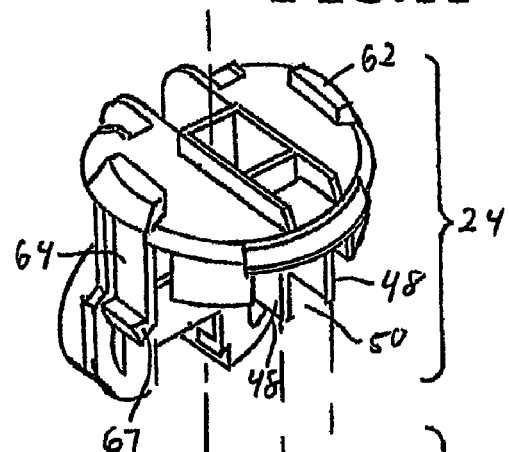
Figure 12:
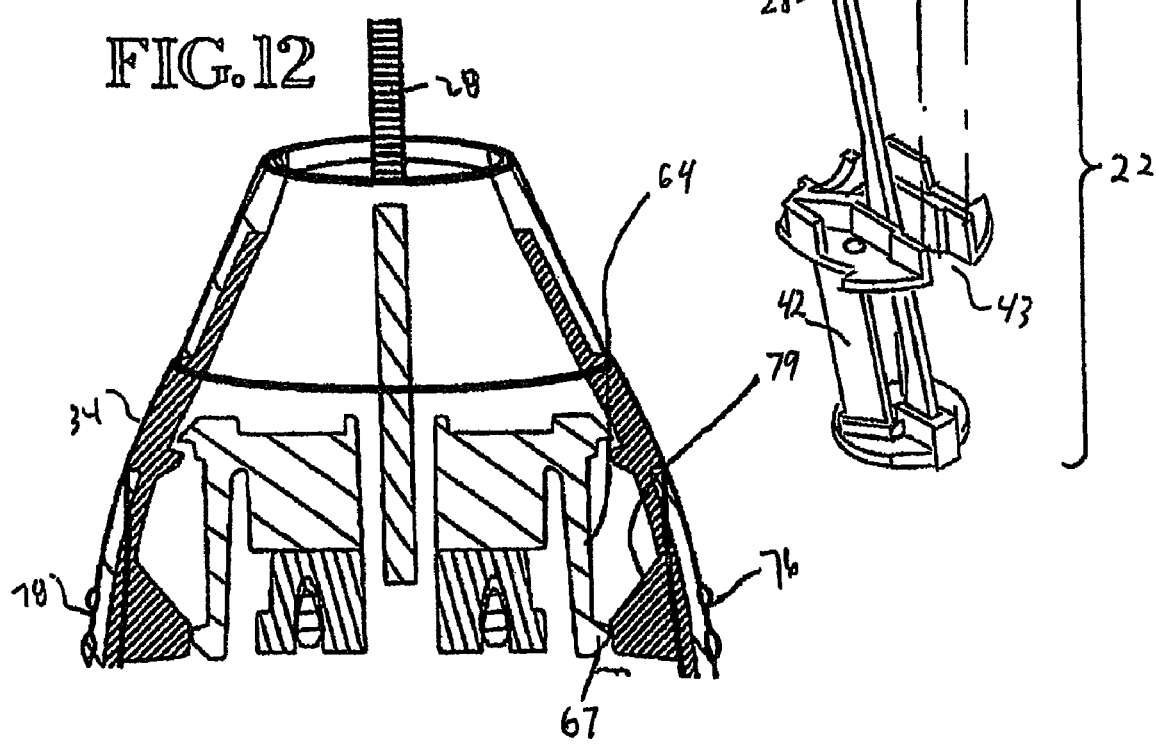
FIG. 12 is a cross-sectional view of a portion of the toothbrush of FIGS. 1-4.

FIG. 1 shows a power toothbrush which incorporates the brushhead attachment system of the present invention. The toothbrush as a whole is referred to generally at 10. The toothbrush 10 includes a conventional handle unit 12, with a driving assembly 14 contained therein. The driving assembly can be various kinds, including, but not limited to, the assembly shown in co-pending U.S. patent application Ser. No. 10/137,962, now U.S. Pat. No. 7,067,945, owned by the assignee of the present invention. However, it should be understood that other driving arrangements could be conveniently used, including various electric motor arrangements and fluid-driven arrangements.

At the top end 16 of handle 12 is a cup member 18. Cup member 18 can either be an integral part of handle 12 or a separate unit therefrom which is fixedly secured to the handle. Cup member 18 can generally take various configurations designed to accommodate or interface with the particular driving assembly used in the toothbrush 10. The upper portion 19 of the cup is configured in a particular way to receive the brushhead attachment system of the present assembly. The actual configuration of cup member 18 is described in more detail below.

Secured to cup member 18 is a combination of a spring assembly 22 and carrier assembly 24. The spring assembly and carrier assembly, referred to hereafter as a spring/carrier combination 26, are fitted together and then are secured as a unit to cup member 18. Spring assembly 22, carrier assembly 24 and the upper portion 19 of cup member 18 are configured in a particular way to define the brushhead attachment assembly of this invention. Spring assembly 22 includes a rigid mounting arm 28, which extends upwardly from the remainder of the spring assembly. Mounted on mounting arm 28 is a brush member assembly 30, which includes a brush unit 31. Brush member assembly 30 moves in a manner determined by the arrangement of spring assembly 22 and the driving assembly 14 to clean the user's teeth. The particular action of the brush member assembly, however, is not a part of the present invention. A plurality of different brush member driving arrangements, with different resulting brush movement, can be used with the present invention. Spring assembly 22 is shown and described having a particular arrangement and configuration. The brushhead attachment system of the present invention, however, can be used with a wide variety of similar structures on electric toothbrushes. The invention is not limited to the particular spring assembly shown. The combination of the spring/carrier assembly and the brush member assembly defines the brushhead assembly portion of the toothbrush 10.

Positioned between the lower end of brush member assembly 30 and the top end 16 of handle 12 is an upper housing 34 (FIG. 1), which covers the exposed portion of cup member 18 and the upper portions of the spring and carrier combination 26 which extend above the top of cup member 18. The shape of the housing 34 will vary, depending upon the particular structure of the spring/carrier combination 26. In the arrangement shown, but not necessarily, carrier assembly 24 has mounted thereon a small pump unit (not shown) by means of a pump holder 37, the pump being used to move dentifrice from a reservoir (not shown) to the brushhead portion. This arrangement results in a slightly bulging shape of the housing 34. The present invention is useful in a fluid-dispensing application or a non-fluid-dispensing application.

The spring/carrier combination 26 is shown in more detail in FIGS. 2-4, 8 and 11. Spring assembly 22 is designed to convert a side-to-side magnetic driving force from driving assembly 14 into a partial rotational action of mounting arm 28 (and hence brush member assembly 30). Spring assembly 22 includes a base member 36 and an upper member 38, with the base member and the upper member being connected by two flat spring members 40 and 42 set at a preselected angle relative to each other. Mounting arm 28 is mounted in base member 36 and extends upwardly through a slot opening 43 in upper member 38, i.e. it is not secured to the upper member, permitting the mounting arm to rotate freely back and forth through a selected angle.

Carrier assembly 24 is designed to mate with spring assembly 22 to form the spring/carrier combination 26. When carrier assembly 24 and spring assembly 22 are mated together, they are secured by means of two spaced screws 40, 41. Spring assembly 22 has a slot 43 thereon, as previously mentioned, through which mounting arm 28 extends. One section of carrier assembly 24 includes a base portion 47 and depending wall members 48, which fit adjacent the inner surface of slot 43 in the spring assembly, which thus decreases the width of slot 43. The depending wall members 48 are configured to define an opening 50 of selected dimension, in this case, approximately 3.2 mm wide by 3.2 mm deep.

The dimensions of opening 50 coincide with but are slightly smaller than vertical rib 52 which extends down the inside surface of cup 18 and which fits into opening 50. The fit between rib 52 on cup 18 and opening 50 in the carrier assembly is thus an interference-type fit which prevents rotational movement of the spring/carrier combination (and hence the brushhead assembly) relative to the handle, but such that it is still relatively easy for the average user to conveniently remove the carrier/spring combination from the cup member 18, such as when it is time to replace the brushhead assembly.

In the embodiment shown, cup member 18 includes a cutout portion 54 extending downwardly from a top edge 56 thereof. In the embodiment shown, cutout portion 54 is on the opposite side, i.e. 180° removed from, rib portion 52, although this is not necessary, i.e. cutout portion 54 could be at other positions around the periphery of the cup member. Cutout portion 54 has a single "stair-step" side edge configuration, such that it is approximately 19 mm wide at the top edge thereof, with the side edges extending downwardly slightly more than 3.2 mm at that width, at which point the width of the cutout portion decreases to approximately 9.76 mm, with the side edges then extending downwardly another 6.4 mm to the bottom edge of the cutout portion.

The carrier assembly includes a portion 58, which extends downwardly from a top edge thereof, to engage the cutout portion 54. When the spring/carrier combination 26 is fitted into cup member 18, portion 58 of the carrier assembly fits snugly into cutout portion 54 on the cup member. The configuration of the cutout portion 54 and portion 58 can of course be varied significantly as well as their position around the peripheries of cup member 18 and carrier assembly, respectively. The fit, however, between portion 58 of the carrier assembly and cutout portion 54 on the cup member 18 serves to prevent rotation of the spring/carrier combination and also, because of the snugness of their fit, provides some protection against translational (in/out) movement of the spring/carrier combination relative to the handle, while at the same time permitting the spring/carrier combination and the brush member structure associate thereon to be conveniently removed from cup 18 when it is time to replace the brush.

Also extending down from the top edge of carrier assembly 24 are two carrier snap (spring) fingers 62 and 64. In the embodiment shown, carrier spring fingers 62 oppose each other, i.e. are 180° apart, and are located orthogonal (at 90°) relative to portion 58 on the carrier assembly. However, the carrier spring fingers 62, 64 could be located at different positions around the periphery of the cup 18 and furthermore need not oppose each other. Still further, one spring finger could be used. The embodiment disclosed, however, is the most convenient and efficient arrangement presently known.

The spring fingers 62, 64 are joined, respectively, to the carrier assembly at their top edges in a resilient, hinge-like arrangement. This permits the lower ends of snap fingers 62, 64 to move slightly in and out, toward and away from the carrier assembly about the hinge joint, i.e. the snap fingers can be moved inwardly under a small force, but move outwardly into a normal position when the force is released. At the lower end of carrier spring fingers 62, 64 are outwardly extending ear portions 66, 67. Mating openings 70, 71 are provided in the wall 69 of cup member 18 in the same relative position as the spring fingers 62, 64 on carrier assembly 24. Narrow slots 63, 65 extend from the openings to the top edge of the cup member 18. The ear portions 66, 67, respectively, on spring fingers 62, 64 are configured relative to openings 70, 71 in cup 18 such that when the carrier/spring combination is positioned operatively within cup 18, the ear portions 66, 67 extend through openings 70, 71 in the cup.

The carrier spring fingers 62, 64 have a springing action about their connecting joints, as discussed above, tending to move outwardly, such that as the spring/carrier combination is moved downwardly into cup 18, the ear portions are forced slightly inwardly, and when the ear portions come adjacent openings 70, 71, the spring action of the spring fingers force ear portions 66, 67 into and partially through openings 70, 71. By this arrangement and action, the spring/carrier assembly is held strongly against any translational (in and out) movement relative to cup 18 and hence handle 12 as well.

Bell release buttons 76 and 78, provided on the opposing sides of housing 34, each have a portion 79 which extends into contact with the ear portion 66, 67 of the spring fingers when the ear portion extend through openings 70, 71. Pushing inwardly on the buttons 76 and 78 releases the ear portions from their openings, so that only a relatively small pulling force on the brushhead assembly is sufficient to remove the brushhead assembly from the cup member 18.

In the embodiment shown and described, the combination of (1) the snug fit between opening 50 defined by the spring/carrier combination and rib 52 in cup member 18, (2) cutout portion 54 in the wall of cup 18 and portion 58 on carrier assembly 24 and (3) snap (spring) fingers 62 and 64 fitting into mating openings 70 and 71 in the cup 18 prevent both rotational action of the brush member assembly relative to the handle and translational action between those two elements as well.

Hence, a system has been shown and described which provides a secure attachment between a brushhead assembly and a handle, without requiring any rotational or twisting action to secure the brushhead assembly to the handle. While the arrangement shown has two opposed (180° apart) connections between the spring/carrier combination 26 and the cup member 18, more connections could be used with different angular spacing. Two connections, however, are sufficient; in some cases, one such connection structure is adequate. In the arrangement shown, relatively tight tolerances for the spring/carrier assembly and the cup member need only be present in the connection areas. Otherwise, the fit tolerance can be relatively generous.

Further, while two snap finger/opening combinations are shown, only one is necessary. More than two such combinations, furthermore, are possible, if desired.

An alternative embodiment is shown in FIGS. 5-7. In this embodiment, an external vertical surface 100 of a carrier assembly 102 includes a horizontal rib 104 which extends substantially around the periphery thereof. An upper peripheral section 106 of cup member 107 has a plurality of spaced vertical slots 108 therein, which extend downwardly from an upper edge 110 thereof, a distance of approximately 9.6 mm, thereby defining a plurality of closely spaced finger-like projections 112 around the upper section 106 of the cup. On the inner surfaces of the projections 112 is a groove 114 into which the rib 104 from the carrier assembly can fit. Once rib 104 mates with groove 114, it is difficult to move the brushhead in a translational (in and out) action relative to the handle. Significant force is typically required to overcome the mating action of the carrier rib and the cup groove, such as to replace the brushhead assembly. The embodiment of FIGS. 5-7 also includes structure similar to the spring/carrier opening and cup rib combination and the cup cutout/carrier portion structure to prevent rotational action of the brushhead assembly and the handle.

Although a preferred embodiment of the invention has been disclosed for purposes of illustration, it should be understood that various changes, modifications and substitutions might be incorporated in the embodiment without departing from the spirit of the invention, which is defined by the claims which follow.

What is claimed is:

1. A power toothbrush, comprising:
a brushhead assembly, the brushhead assembly including a mounting shaft on which is positioned a brush bristle unit for brushing teeth and a force conversion assembly adapted and arranged to convert a driving force into a movement of the mounting shaft to move the bristle unit to accomplish cleansing of the teeth, wherein the force conversion assembly comprises a combination of a spring assembly which is responsive to a driving force to move the mounting shaft, and a carrier assembly which engages the receiving portion of the handle;
a handle to which the brushhead assembly is removably attached, the handle having a fixed receiving portion, which includes an upper hollow portion into which a lower part of the force conversion assembly fits; and
an attachment system which includes a first connection arrangement comprising a part on the hollow portion of the fixed receiving portion and a corresponding mating part on the force conversion assembly for positively preventing rotational movement of the brushhead assembly relative to the handle; wherein the force conversion assembly further includes at least one engaging member which, when the brushhead assembly is operatively positioned in the receiving portion, extends at least partially into an opening in the receiving portion of the handle, which positively prevents translational movement of the brushhead assembly relative to the handle during operation of the toothbrush, wherein the attachment system is configured and arranged such that the brushhead assembly is removed from the handle or inserted into the handle linearly, directly toward and away from the handle, without rotation of the brushhead assembly being necessary to tighten the brushhead assembly onto the handle or loosen it therefrom.

2. The power toothbrush of claim 1, wherein the spring assembly/carrier assembly combination includes two opposing spring finger members which depend downwardly from an upper edge thereof, mating securely with two associated openings in the receiving portion to prevent translational movement of the brushhead assembly relative to the handle.

3. The power toothbrush of claim 2, wherein each spring finger member includes an ear portion at a lower end thereof which fits into its associated opening in the receiving portion.

4. The power toothbrush of claim 3, wherein the brushhead assembly further includes a housing portion and wherein the attachment system includes a disengaging member mounted in the housing and movable such that it acts against the engaging member present in the opening, forcing it out of the opening, so that the brushhead assembly can be readily moved away from the receiving portion.

5. The power toothbrush of claim 1, wherein the first connection arrangement includes an opening in a wall portion of the force conversion combination, adapted to mate snugly with a rib portion on an internal surface of the receiving portion of the handle.

6. The power toothbrush of claim 1, wherein the carrier assembly includes a portion thereof adapted to carry a fluid pump for moving fluid from a reservoir to the bristle unit.

7. The power toothbrush of claim 1, wherein the first and second connection arrangements approximately oppose each other around the peripheries of the receiving portion and the force conversion assembly.

8. A power toothbrush, comprising:
a brushhead assembly;
a handle to which the brushhead assembly is removably attached, the handle having a fixed receiving portion, the brushhead assembly including a force coupling assembly adapted and arranged to couple a driving force produced by a driver portion of the power toothbrush to a mounting shaft on which a set of bristles is mounted, wherein the fixed receiving portion includes an upper hollow portion into which a lower portion of the force coupling assembly fits; and
a brushhead attachment system, wherein the force coupling assembly includes a slot therein into which a rib member on an internal surface of the hollow portion of the fixed receiving portion of the handle snugly fits to positively prevent rotational movement of the brushhead assembly relative to the handle and wherein the force coupling assembly includes at least one engaging member which, when the brushhead assembly is operatively positioned in the receiving portion of the handle, extends at least partially into an opening in the receiving portion, to positively prevent translational movement of the brushhead assembly relative to the handle during operation of the toothbrush, wherein the engaging member includes a part at a lower end thereof which fits into said opening in the receiving portion, and wherein the brushhead assembly further includes a housing portion therefor, the attachment system including a disengaging member mounted in said housing portion and moveable such that it is actionable by a user against the engaging member part present in the opening, forcing it out of the opening, so that the brushhead assembly can be readily moved away from the receiving portion.

9. The power toothbrush of claim 8, wherein the attachment system is configured and arranged to permit the brushhead assembly to be removed from the handle or inserted into the handle in a linear movement thereof, without rotation of the brushhead assembly.

* * * * *